United States Patent
Katayama

(10) Patent No.: US 9,452,869 B2
(45) Date of Patent: *Sep. 27, 2016

(54) CONTAINER WITH LIQUID SQUEEZE NOZZLE

(76) Inventor: Ryu Katayama, Tokyo (JP)

( * ) Notice: Subject to any disclaimer, the term of this patent is extended or adjusted under 35 U.S.C. 154(b) by 1259 days.

This patent is subject to a terminal disclaimer.

(21) Appl. No.: 12/353,643

(22) Filed: Jan. 14, 2009

(65) Prior Publication Data

US 2009/0137972 A1    May 28, 2009

Related U.S. Application Data

(63) Continuation of application No. PCT/JP2007/063925, filed on Jul. 12, 2007.

(30) Foreign Application Priority Data

Jul. 14, 2006   (JP) .................. 2006-193533

(51) Int. Cl.
| | |
|---|---|
| B65D 47/18 | (2006.01) |
| B05B 11/04 | (2006.01) |
| B05B 11/00 | (2006.01) |
| B65D 47/20 | (2006.01) |

(52) U.S. Cl.
CPC ........... B65D 47/18 (2013.01); B05B 11/0072 (2013.01); B05B 11/303 (2013.01); B05B 11/3032 (2013.01); B05B 11/3094 (2013.01); B65D 47/2031 (2013.01)

(58) Field of Classification Search
CPC ........................... B65D 41/06; B05B 11/0075
USPC .................. 604/294–302; 222/207, 420, 422
See application file for complete search history.

(56) References Cited

U.S. PATENT DOCUMENTS

| | | | | | |
|---|---|---|---|---|---|
| 996,330 | A | * | 6/1911 | Haines | 222/207 |
| 1,428,969 | A | * | 9/1922 | Midson | 215/332 |
| 1,595,187 | A | * | 8/1926 | Grayson | 222/92 |
| 2,219,604 | A | * | 10/1940 | Trotter | 222/207 |
| 2,662,724 | A | * | 12/1953 | Kravagna | F16K 15/147 |
| | | | | | 137/847 |
| 2,734,665 | A | * | 2/1956 | Flamm | 222/207 |
| 2,754,027 | A | * | 7/1956 | Schulte | 220/291 |
| 2,811,283 | A |  | 10/1957 | Bowen | |
| 2,979,236 | A | * | 4/1961 | Fahr | 222/207 |
| 3,180,532 | A | * | 4/1965 | Michel | 222/182 |

(Continued)

FOREIGN PATENT DOCUMENTS

| | | | |
|---|---|---|---|
| EP | 1 561 699 A1 | 10/2005 | |
| EP | 2003069 A2 | 12/2008 | |

(Continued)

*Primary Examiner* — Paula L. Craig
(74) *Attorney, Agent, or Firm* — Baker & Hostetler LLP

(57) ABSTRACT

A container (1) with a liquid-squeezing nozzle has a main body (2) having an opening (21) and collecting liquid (L), a nozzle (3) mounted on the opening (21), and a cap (4) covering the nozzle (3) and being mounted on main body (2) removable. The nozzle (3) has a storage part (33), a liquid supplying path (34), and a valve (35). The storage part (33) has rubber elasticity, and collects liquid (L) without posture of the main body (2). The liquid supplying path (34) communicates from the opening (21) to the storage part (33). The valve (35) is usually shut, and is opened to spout liquid (L) of the storage part (33) when internal pressure of the storage part (33) exceeds constant pressure by shutting the communication between the storage part (33) and the liquid supplying path (34).

10 Claims, 7 Drawing Sheets

(56) References Cited

U.S. PATENT DOCUMENTS

| | | | | |
|---|---|---|---|---|
| 3,323,689 | A | * | 6/1967 | Elmore .................... 222/385 |
| 3,366,284 | A | * | 1/1968 | Marona et al. ............ 222/211 |
| 3,552,605 | A | * | 1/1971 | Hein ........................ 222/207 |
| 3,645,423 | A | * | 2/1972 | DeGraw .................... 222/207 |
| 3,667,636 | A | * | 6/1972 | Landen .................... 215/214 |
| 3,680,745 | A | * | 8/1972 | Landen .................... 222/570 |
| 3,752,366 | A | * | 8/1973 | Lawrence, Jr. ............ 222/207 |
| 3,756,732 | A | | 9/1973 | Stoffler |
| 3,822,720 | A | * | 7/1974 | Souza ...................... 137/846 |
| 3,888,251 | A | | 6/1975 | Harrison |
| 4,101,057 | A | | 7/1978 | Lomaglio |
| 4,111,200 | A | * | 9/1978 | Sbarra et al. ............ 604/298 |
| 4,153,172 | A | * | 5/1979 | Bialobrzeski ............ 215/209 |
| 4,416,308 | A | * | 11/1983 | Bower .................. B65D 31/14 137/846 |
| 4,526,490 | A | * | 7/1985 | Welsh ...................... 401/183 |
| 4,538,740 | A | * | 9/1985 | Petersen, Jr. ............ 215/246 |
| 4,545,510 | A | * | 10/1985 | Mettenbrink ............ 222/209 |
| 4,553,686 | A | | 11/1985 | Dougherty |
| 4,568,004 | A | * | 2/1986 | Goncalves ................ 222/207 |
| 4,792,334 | A | | 12/1988 | Py |
| 4,903,867 | A | * | 2/1990 | Mettenbrink ............ 222/207 |
| 5,069,675 | A | | 12/1991 | Menchel et al. |
| 5,261,571 | A | * | 11/1993 | Goncalves ................ 222/214 |
| 5,301,707 | A | * | 4/1994 | Hofsteenge ........ F16K 15/147 137/12 |
| 5,303,851 | A | | 4/1994 | Libit et al. |
| 5,356,039 | A | * | 10/1994 | Christine et al. ........ 222/107 |
| 5,578,020 | A | * | 11/1996 | Mosley .................... 604/295 |
| 5,582,330 | A | | 12/1996 | Iba |
| 5,810,203 | A | * | 9/1998 | Brennan .................. 222/207 |
| 5,810,794 | A | | 9/1998 | Peplinski |
| 6,092,551 | A | * | 7/2000 | Bennett .............. F16K 15/147 137/843 |
| 6,135,985 | A | * | 10/2000 | Fromer .................... 604/295 |
| 6,168,581 | B1 | * | 1/2001 | Buehler .................... 604/295 |
| 6,450,375 | B1 | * | 9/2002 | Hins ................ B65D 47/2031 222/484 |
| 6,595,970 | B1 | * | 7/2003 | Davidian .................. 604/300 |
| 6,612,469 | B2 | * | 9/2003 | Lopez Pardo ............ 222/214 |
| 6,814,265 | B2 | | 11/2004 | Clifford et al. |
| 7,063,687 | B2 | | 6/2006 | Benktzon et al. |
| 7,077,831 | B2 | | 7/2006 | Skolik |
| 7,353,971 | B2 | | 4/2008 | Stradella |
| 7,635,070 | B2 | | 12/2009 | Cohen et al. |
| 7,828,176 | B2 | * | 11/2010 | Harper .................... 222/207 |
| 8,496,635 | B2 | * | 7/2013 | Katayama ................ 604/298 |
| 2002/0079338 | A1 | * | 6/2002 | Pardo ...................... 222/422 |
| 2002/0190079 | A1 | * | 12/2002 | Hamamoto .............. 222/105 |
| 2003/0047937 | A1 | * | 3/2003 | Chaduc et al. ............ 283/81 |
| 2004/0262339 | A1 | * | 12/2004 | Stradella .................. 222/633 |
| 2005/0165368 | A1 | * | 7/2005 | Py et al. .................. 604/289 |
| 2005/0173468 | A1 | * | 8/2005 | Matsumoto et al. ...... 222/494 |
| 2005/0258131 | A1 | * | 11/2005 | Moser ...................... 215/246 |
| 2006/0037968 | A1 | * | 2/2006 | Brenner .................... 222/105 |
| 2006/0111680 | A1 | * | 5/2006 | Spada et al. .............. 604/295 |
| 2007/0093765 | A1 | * | 4/2007 | Kawashiro et al. ...... 604/295 |
| 2009/0137972 | A1 | | 5/2009 | Katayama |
| 2009/0318883 | A1 | | 12/2009 | Sugahara et al. |
| 2011/0106024 | A1 | * | 5/2011 | Katayama ................ 604/294 |

FOREIGN PATENT DOCUMENTS

| | | |
|---|---|---|
| JP | 0013045 Z1 | 5/1909 |
| JP | T13-003803 Y1 | 10/1924 |
| JP | 62-120859 A | 6/1987 |
| JP | 63101961 A1 | 5/1988 |
| JP | 64003045 A1 | 1/1989 |
| JP | 02023381 A1 | 1/1990 |
| JP | 05-034663 Y2 | 9/1993 |
| JP | 5-91680 U | 12/1993 |
| JP | 6-292703 A | 10/1994 |
| JP | 7-3645 U | 1/1995 |
| JP | 7-204269 A | 8/1995 |
| JP | 2000-210368 A | 8/2000 |
| JP | 2001003803 A1 | 1/2001 |
| JP | 2001-122284 A | 5/2001 |
| JP | 2002-191671 A | 7/2002 |
| JP | 2003-319999 A | 11/2003 |
| JP | 2004 001829 A | 1/2004 |
| JP | 2004-148052 A | 5/2004 |
| JP | 2004210313 A1 | 7/2004 |
| JP | 2005335773 A1 | 12/2005 |
| JP | 2006-124016 A | 5/2006 |
| JP | 200818987 A1 | 1/2008 |
| WO | 9811852 A1 | 3/1998 |
| WO | 02094069 A1 | 11/2002 |
| WO | 2007111256 A1 | 10/2007 |

* cited by examiner

CONTAINER WITH LIQUID SQUEEZE NOZZLE

CROSS-REFERENCE TO RELATED APPLICATIONS

This application is based upon and claims the benefit of priority from the prior Japanese Patent Application No. 2006-193533, filed Jul. 14, 2006 and International Application No. PCT/JP2007/063925, filed Jul. 12, 2007, the entire contents of which are incorporated herein by reference.

BACKGROUND OF THE INVENTION

1. Field of the Invention

The present invention relates to the container with the liquid-squeezing nozzle including the nozzle that spouts the liquid little.

2. Description of the Related Art

The applying eyewash container includes a container where liquid medicine is collected and a nozzle that drops liquid medicine. The nozzle is arranged in the top of the container. The container is made upside-down and used so that the nozzle may turn below when liquid medicine is applied with this eye drops container. The user comes to look up at the liquid medicine that is ejected from the nozzle by pressing the container and added dropwise. However, it should become accustomed to add the liquid medicine dropwise to the eyeball well with it saw right above. Moreover, when it is difficult to face up, liquid medicine cannot be applied eyewash well. Then, the applying eyewash container to supply liquid medicine to eyes even if not looking up is disclosed in Jpn. Pat. Appln. KOKAI Publication No. JP H07-204269 A, JP H06-292703 A, JP 2002-191671 A, JP 2000-210368 A, JP 2003-319999 A, and JP 2004-148052 A, and Jpn. UM. Appln. KOKAI Publication No. JP H05-91680 U, and JP H07-3645 U.

The applying eyewash container described in Jpn. Pat. Appln. KOKAI Publication No. JP H07-204269 A and JP H06-292703 A apply the nozzle of the spray. The applying eyewash tool described in Jpn. UM. Appln. KOKAI Publication No. JP H05-91680 U is installed in the top of the container, and the nozzle extends diagonally. Liquid medicine is filled in the applying eyewash tool with the container made inverted. When the edge wall part is pressed and dented, liquid medicine is flowed out from the nozzle.

The applying eyewash container where liquid medicine is spouted from the nozzle by improving the internal pressure pushing the container from the outside by the finger is described in Jpn. Pat. Appln. KOKAI Publication No. JP 2002-191671 A. This applying eyewash container comprises the pocket that collects liquid medicine in the upstream part of the nozzle in posture in which the container is made to stand up. The applying eyewash container described in Jpn. UM. Appln. KOKAI Publication No. JP H07-3645 U comprises reservoir instead of the pocket. This reservoir is arranged at a position that is higher than a liquid surface inside in the container, and opens to transverse. The staple is installed in the opening, and liquid medicine is kept to the reservoir by the surface tension. The bend provided on the body of the container dents internally momentarily by exceeded a certain position when it is pressed. Liquid medicine is spouted from the nozzle by the power at that time.

The applying eyewash container described in Jpn. Pat. Appln. KOKAI Publication No. JP 2000-210368 A has the cylinder having a spout hole, the valve, and the spring in the nozzle. Liquid medicine with reservoir provided in the upstream of the nozzle spouts from the nozzle when the container is pressed. At this time, since the cylinder moves according to the internal pressure, and channel of the valve communicates the inside and the outside of the container, the container has the structure to spout liquid medicine at a dash.

The eyedropper described in Jpn. Pat. Appln. KOKAI Publication No. JP 2003-319999 A has the means to eject the drop of water momentarily. This means to eject the drop of water momentarily has the main body of a cylindrical sliding button and the piston inserted in the main body. The cam is provided between the main body of the sliding button and the piston, and the piston spring is inserted in. When the main body of the sliding button is pushed, and the cam is released, the piston is extruded by the piston spring at a dash. The fixed quantity mass part is provided in the tip of the extruded piston. Channel to the container side is intercepted with the piston, and the liquid medicine collected in the fixed quantity mass part is spout from the discharge opening of the applying eyewash liquid. Besides this, the embodiment to which liquid medicine spouts by moving the piston by flatness it as for the container adding the internal pressure and the embodiment spouted by using the air compressed with the pump are disclosed in Jpn. Pat. Appln. KOKAI Publication No. JP 2003-319999 A.

The adaptor for the eyedropper described in Jpn. Pat. Appln. KOKAI Publication No. JP, 2004-148052, A is installed in the opening of the container which drops the droplet. The adaptor for the eyedropper provides the spout part on the way of the liquid path that leads from the opening to the nozzle. The spout part halves the communication path that runs to the liquid path, and spouts liquid medicine in the liquid path from the communication path to the nozzle by pressing the spout part with the finger.

However, when the button is pressed with the finger to spout liquid medicine, the hand moves, and the applying eyewash container of the spray described in Jpn. Pat. Appln. KOKAI Publication No. JP H07-204269 A and JP H06-292703 A might not be able to be sprayed to eyes well. The applying eyewash tool described in Jpn. UM. Appln. KOKAI Publication No. JP H05-91680 is located below when the edge wall part that should press uses it, and not operated easily. Moreover, the liquid might drip according to pressing strength. In the applying eyewash container described in Jpn. Pat. Appln. KOKAI Publication No. JP 2002-191671, the internal pressure that spout liquid medicine is insufficient, and liquid medicine drips from the nozzle if the container is not instantaneously pressed with the finger. Liquid medicine might flow out from the nozzle by just that much since the container is flat gradually of it until the bend is displaced even in case of the applying eyewash container described in Jpn. UM. Appln. KOKAI Publication No. JP H07-3645 and Jpn. Pat. Appln. KOKAI Publication No. JP 2004-148052.

Each applying eyewash container described in Jpn. Pat. Appln. KOKAI Publication No. JP 2000-210368 and JP 2003-319999 have the complication mechanism, and it is uneconomical as the throw container, considering assembling these.

BRIEF SUMMARY OF THE INVENTION

The present invention provides a container with a liquid-squeezing nozzle that can squirt a small amount of liquid without depending on posture and can manufacture it from a simple structure at a low price.

A container with a liquid-squeezing nozzle according to the present invention comprises a main body having an opening and collecting a liquid, a nozzle mounted on the opening, and a cap covering the nozzle and mounted on the main body removable. The nozzle has a storage part, a liquid supplying path, and a valve. The storage part is provided in the tip where it had the rubber elasticity, and collects the liquid without depending on the posture of the main body. The liquid supply path communicates from the opening to the storage part. The valve is usually shut, and is opened to squirt the liquid of the storage part when the internal pressure of the storage part exceeds constant pressure by closing the communication between the storage part and the liquid supplying path.

In this case, the nozzle preferably comprises a conduit tube that extends from the liquid supplying path to the inside of the main body further. Moreover, the nozzle preferably has a protrusion that shuts communication between the liquid supplying path and the storage part with the liquid made to stay in the storage part in case of flatness.

The valve is composed by a slit which fits to be closed and has width for a squirt direction of the flow of the liquid. The valve is composed by a cross slit which fits to be closed and has width for the squirt direction of the flow of the liquid. In this case, the valve forms the fitting part longer than the width of the slit for the squirt. Or, the valve is a pin-sized hole to be expanded to open when the internal pressure of the storage part exceeds constant pressure, and to make the liquid in the storage part squirt.

The container with the liquid-squeezing nozzle of other embodiments further comprises the lever. The lever is provided in the couple at the position of symmetry that centers on the nozzle, and the each lever is extends toward the valve side being supported to the position of the opening side. Moreover, the lever has flexibility, and squeezes up the storage part from the side of the liquid supplying path by displacing in the direction where the nozzle is placed toward the valve.

The container with the liquid-squeezing nozzle of the present invention comprising the above-mentioned structure can spout the liquid in the main body little without depending in the direction of the nozzle. The container with the liquid-squeezing nozzle of the present invention can spout a small amount of liquid measure from the nozzle from one drop defined by the surface tension. Therefore, when the container with the liquid-squeezing nozzle of the present invention is used as an applying eyewash container, the user comes to be able to apply liquid medicine in the posture that faces to the front or down without looking up at above. In a word, since the content fluid can be spouted without it is influenced by gravity, even the person who is difficult to look up at above could apply eyewash easily, and it can apply eyewash in the zero gravity environments.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the Invention

Figure 1:
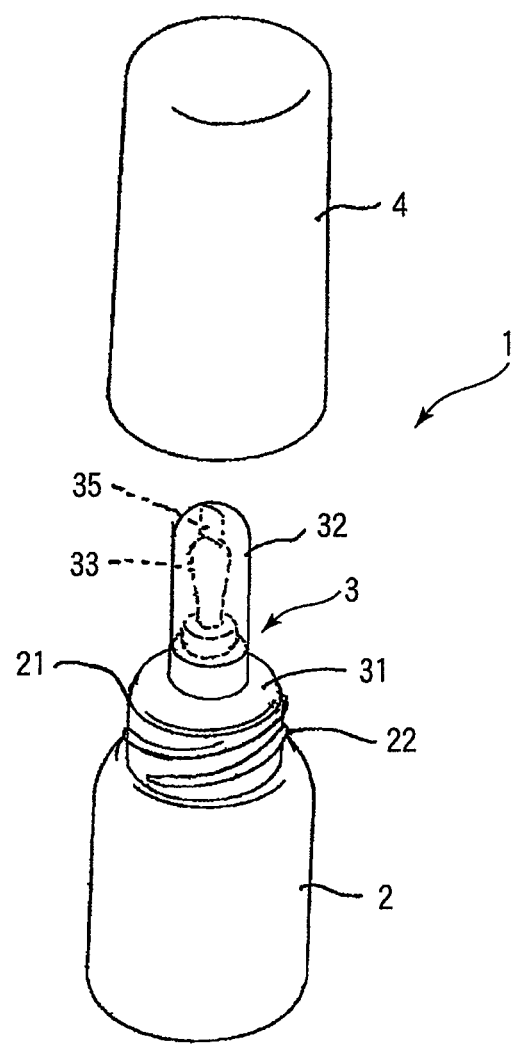
FIG. 1 is exploded perspective view of the container with the liquid-squeezing nozzle according to the first embodiment of the invention.

A container 1 with a liquid-squeezing nozzle of the first embodiment of the invention will be described as an example of the case where it is used as an applying eyewash container with reference to FIG. 1 to FIG. 5. The container 1 with the liquid-squeezing nozzle shown in FIG. 1 comprises a main body 2, a nozzle 3, and a cap 4. The main body 2 has an opening 21 and collects liquid L that is liquid medicine internally. It is preferable that the main body 2 is formed with plastic like the material etc. that are not deteriorated by internal liquid L, do not begin to melt to liquid L of contents and do not ruin the grade of this liquid L, such as the glass and the polypropylene.

The nozzle 3 is mounted on the opening 21. After liquid L is put in the main body 2, the nozzle 3 is fixed by the method not to drop out from the opening 21 easily. In this embodiment, it is pressed in. It may be bonded after the nozzle 3 is pressed in, and when the main body 2 and the nozzle 3 are plastics, these are fused together mutually by the laser or the ultrasonic wave. The cap 4 is screwed together as a screw 22 formed in outer in the opening 21, and covered to protect the nozzle 3. Since the cap 4 only has to be attached to cover the nozzle 3 with the structure that could not be easily removed, it may be a structure that engages outside on the opening 21 except screwing together by the screw structure.

Figure 2:
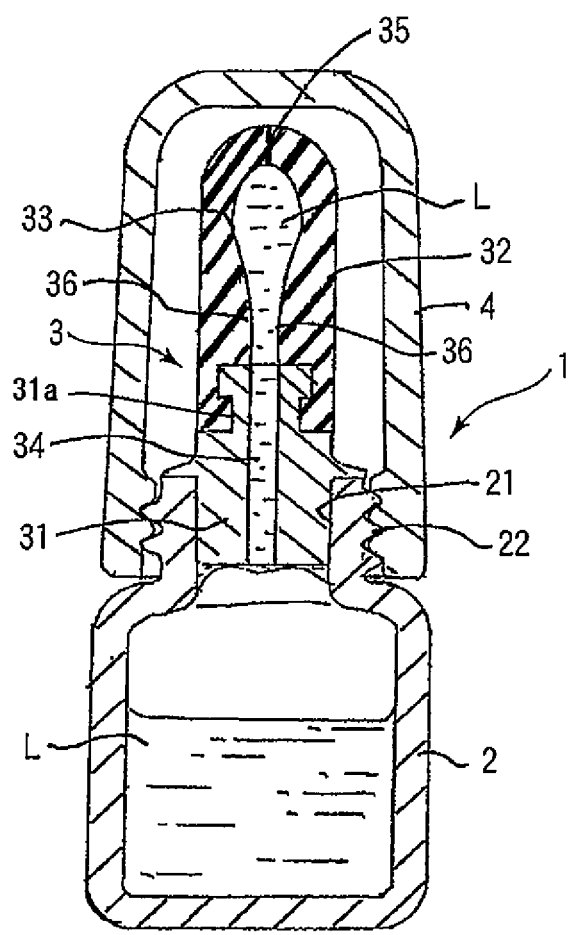
FIG. 2 is cross-sectional view of the container with the liquid-squeezing nozzle shown in FIG. 1.

The nozzle 3 has a base 31 and a constriction part 32 where it had the rubber elasticity, and a storage part 33, a liquid supplying path 34, and a valve 35 are formed to the nozzle 3. The base 31 is engaged into in the opening 21 of the main body 2, and has a groove 31a where constriction part 32 is set in the side and the other side inserted in the opening 21. The storage part 33 is formed in the constriction part 32 as shown in FIG. 2. The storage part 33 is formed with an excellent material in stability when it is flatness repeatedly such as the silicone rubbers and urethane elastomers for instance, and collects liquid L without depending on the posture of the nozzle 3. The constriction part 32 preferably fuses with the base 31, as it not only is engaged but also becoming watertight by the laser or the ultrasonic wave. It is preferable to form integrally the constriction part 32 by the soft material and the base 31 by a hard material by injection molding.

The liquid supplying path 34 is provided in the base 31, and communicates the opening 21 and the storage part 33. The liquid supplying path 34 is formed more narrowly than the storage part 33, to such an extent in which liquid L that entered the storage part 33 is made to remain as it is in the storage part 33 according to the surface tension of the liquid L. A protrusion 36 is formed between the storage part 33 and the liquid supplying path 34. When the constriction part 32 is nipped and is flatness as shown in FIG. 4, the protrusion 36 blocks communication between the storage part 33 and the liquid supplying path 34.

Figure 3:
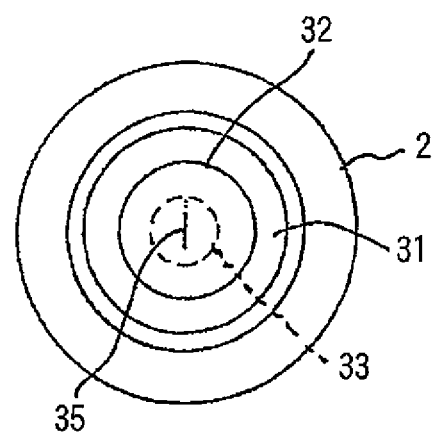
FIG. 3 is a plan view seen from the nozzle tip side of the container with the liquid-squeezing nozzle shown in FIG. 1.

The valve 35 is provided in the tip of the constriction part 32 where is the opposite side of the base 31 as shown in FIG. 1. Communication between the storage part 33 and the liquid supplying path 34 is closed by nipping the constriction part 32 by finger P, and power is put by the finger further to squeeze liquid L out from the storage part 33 as shown in FIG. 4. As a result, the valve 35 opens to deform elasticity as shown in FIG. 4 when the internal pressure of the storage part 33 exceeds constant pressure, and to communicate the storage part 33 to outside. At this time, liquid L of the storage part 33 is squirted outside by the pressure generated by the elastic force in the constriction part 32. The valve 35 is formed to the slit that has width for the direction where liquid L flows by being incised, and the valve 35 usually fits so as to be shut as shown in FIG. 2 and FIG. 3. The width of the valve 35 is smaller than the internal diameter size of the storage part 33.

Figure 4:
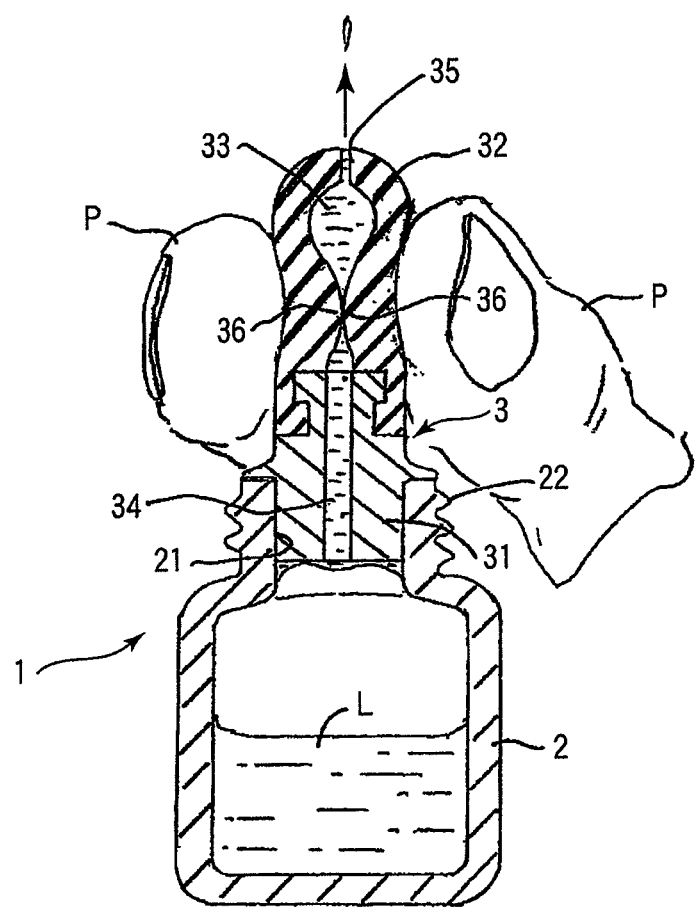
FIG. 4 is cross-sectional view of the state in which the container with the liquid-squeezing nozzle shown in FIG. 2 has been squirting the liquid by being pinched the nozzle by fingers.

When the constriction part 32 is nipped as shown in FIG. 4, the container 1 with the liquid-squeezing nozzle as mentioned above composed seals up between the storage part 33 and the liquid supplying path 34 by the protrusion 36. When power is put in the tip of a finger to begin to squeeze liquid L in the storage part 33 toward the valve 35, the internal pressure of the storage part 33 resists the elastic force of the constriction part 32, and the valve 35 is expanded. Liquid L in the storage part 33 is spouted from the valve 35 in great force since it is pressurized by the elastic force in the constriction part 32.

When liquid L in the storage part 33 is squirted, and the internal pressure of the storage part 33 decreases, the valve 35 is sealed up. In a word, when liquid L in the storage part 33 is discharged, the valve 35 is shut naturally with the constriction part 32 nipped by fingers P. Then, the constriction part 32 restores by the elastic force when fingers are released, and liquid L that is stored in the main body 2 is sucked anew.

Since the liquid L is jetted by the elastic force of the constriction part 32 even if the liquid L in the storage part 33 is a small amount, the liquid L is squirted by droplets smaller than droplets when the liquid L is dripped naturally. Moreover, the liquid L from the tip of the nozzle 3 can be prevented from dripping since the liquid L is mightily jetting from the nozzle 3.

Figure 5:
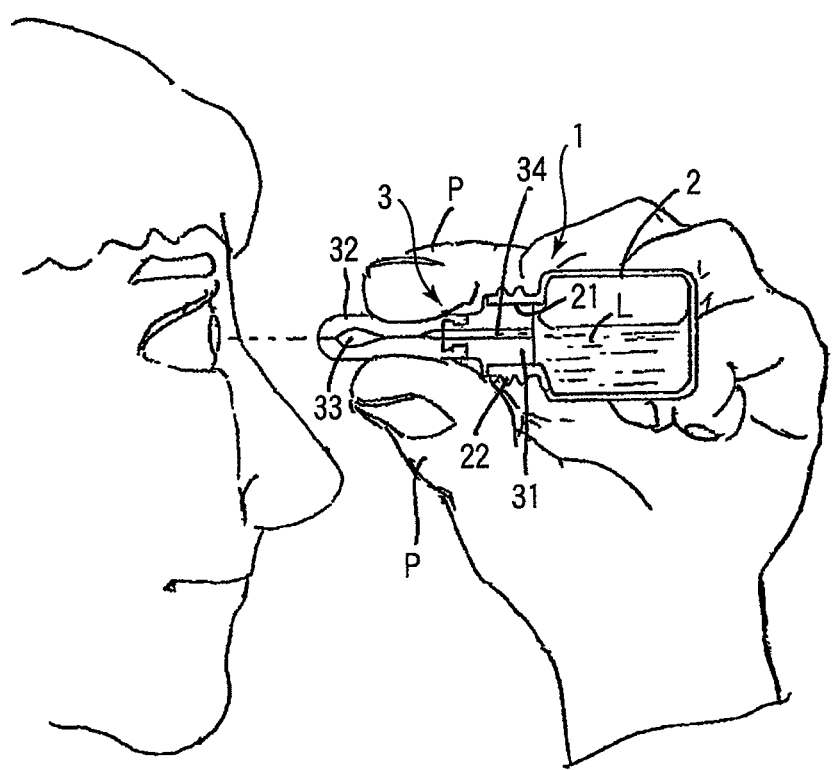
FIG. 5 is partially cross-sectional view of the state in which the container with the liquid-squeezing nozzle shown in FIG. 1 is used as an applying eyewash container.

Therefore, when it uses as an applying eyewash container, the container 1 with the liquid-squeezing nozzle can pour into eyes the liquid L which is liquid medicine stored in the main body 2, even if the container is a sideways posture as shown in FIG. 5. In other word, liquid medicine can be poured into eyes regardless of posture, even if it is difficult to make them drips liquid medicine for a person for whom it is difficult to face above or for the favorite pet.

Therefore, it can apply eyewash while seeing the mirror in the front.

Figure 6:
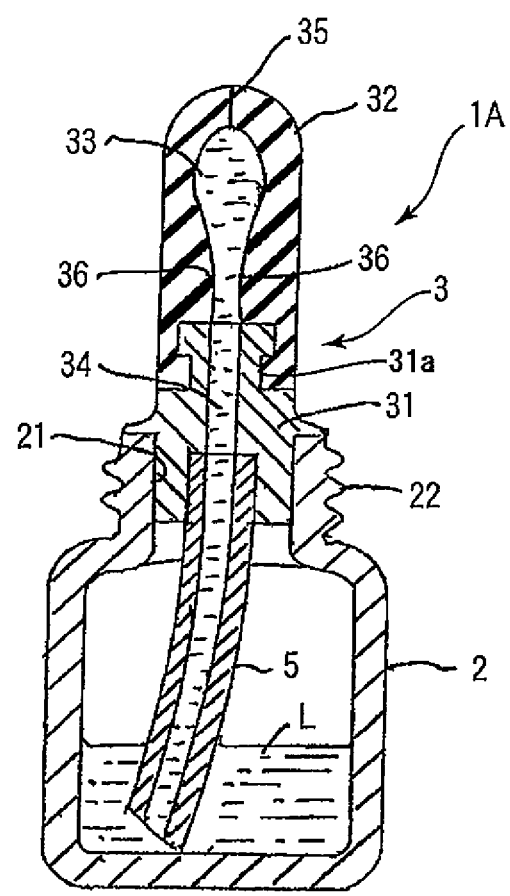
FIG. 6 is cross-sectional view of the container with the liquid-squeezing nozzle according to the second embodiment of the invention.

The container 1A with the liquid-squeezing nozzle of the second embodiment of the present invention will be explained with reference to FIG. 6. The compositions that have the same functions as those in the container 1 with the liquid-squeezing nozzle of the first embodiment are respectively given the same reference symbols, and may omits the description from followings. The cap 4 is omitted in FIG. 6.

The container 1A with the liquid-squeezing nozzle further comprises a conduit tube 5 that has length that extends from the liquid supplying path 34 that opens to the base 31 and gets to the bottom of main body 2. The conduit tube 5 has been inserted in the base 31. Internal liquid L can be sucked up to the storage part 33 by posture in which main body 2 is put up by comprising the conduit tube 5.

The container 1B with the liquid-squeezing nozzle of the third embodiment according to the present invention will be explained with reference to FIG. 7. The compositions that have the same functions as those in the container 1 with the liquid-squeezing nozzle of the first embodiment are respectively given the same reference symbols, and may omits the description from followings. The container 1B with the liquid-squeezing nozzle shown in FIG. 7 equips with a pair of lever 6 at a symmetric position on both sides of the constriction part 32 of the nozzle 3. The levers 6 are fixed to the cover 7 attached on periphery of the opening 21 of main body 2, and extend in parallel to the constriction part 32 toward the valve 35 sides.

Each lever 6 has flexibility, and a bend 61 is formed at the position near the cover 7. Moreover, the lever 6 is formed to shape that near the constriction part 32 in the position near the cover 7, and is gradually away from the constriction part 32 up to the valve 35 sides, so as to squeeze up the constriction part 32 toward the valve 35 by displacing the lever 6 toward the constriction part 32.

The valve 35 is incised and made in cross to intersect the slit where it had width. The valve 35 is shut up as shown in FIG. 7 when the constriction part 32 is not flatness by the lever 6. Liquid L accumulated in the storage part 33 is pressurized when the constriction part 32 is flatness by pinching the lever 6 with the finger, therefore the valve 35 is opened by the pressure.

The shape of the valve 35 may be shape incised like the valve 35 of the first embodiment in one direction. In this case, the valve 35 shows different behavior whether to have width along the direction where a pair of the lever 6 lines up or to have width along the cross direction of the direction where the lever 6 lines up. Therefore, the incised direction is chosen suitably by the elasticity of the constriction part 32 and the viscosity and the amount of liquid L that has been saved in the storage part 33. Moreover, since the straight advancement of jetted liquid L increases, it is prefer that the path length of the valve 35 is provided larger than the width.

Figure 7:
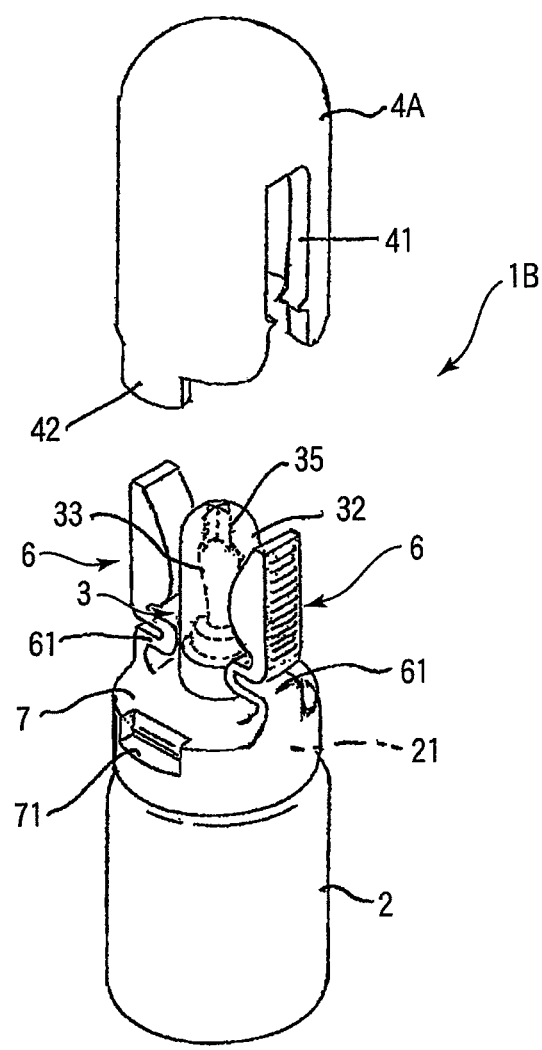
FIG. 7 is exploded perspective view of the container with the liquid-squeezing nozzle according to the third embodiment of the invention.

As shown in FIG. 7, since flatness operation for the constriction part 32 is made constant by comprising the lever 6, the amount and the timing of jetted liquid L are stabilized. Moreover, in this embodiment, the cap 4A includes notches 41 formed so that the lever 6 may be engaged. Furthermore, a recess 71 that engages together with a hook 42 provided in the cap 4A is formed in peripheral of the cover 7. When the cap 4A is detached, the cap 4A is flat according to the operation of the lever 6. Liquid L enters the storage part 33 by doing like this, and it comes to be able to use the container 1B at once.

The container 1C with the liquid-squeezing nozzle according to the fourth embodiment of the present invention will be explained with reference to FIG. 8. The compositions having the same functions as the container 1 with the liquid-squeezing nozzle of the first embodiment and the container 1B with the liquid-squeezing nozzle of the third embodiment are given the same reference symbols and omits the explanation in following.

Figure 8:
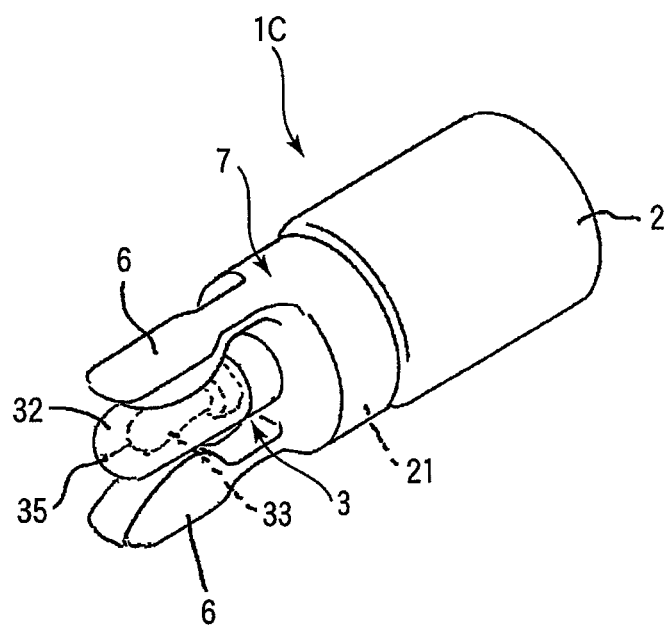
FIG. 8 is exploded perspective view of the container with the liquid-squeezing nozzle according to the fourth embodiment of the invention.

The container 1C with the liquid-squeezing nozzle shown in FIG. 8 has levers 6 in the couple as well as container 1B with the liquid-squeezing nozzle of the third embodiment. However, the lever 6 of this embodiment doesn't have the bend portion. The proximal part of the lever 6 is thinly formed so that it to be easily deflects. Moreover, the valve 35 is formed in a pin-sized hole which is normally narrower and sealed up, and is extended to open by the internal pressure of the storage part 33 when the pressure is exceed the predetermined pressure.

A container with a liquid-squeezing nozzle of the present invention can be used as a container to jet the liquid of a slight amount besides the container of the applying eyewash container, the perfume container and a liquid seasoning containers.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A container with a liquid-squeezing nozzle, comprising:
   a main body, including:
      an opening, and
      an inner cavity to store a liquid;
   a nozzle, mounted on the main body, including:
      a base attached to the opening having a liquid supplying path fluidly communicating with the inner cavity,
      a constriction part having rubber elasticity and flexibility and attached to the base opposite to the main body, the constriction part comprising a storage part configured to store a portion of the liquid and to communicate with the liquid supplying path, a valve which is formed in a slit having a constant width smaller than a path length of the valve and is naturally closed by an elastic force of the constriction part, and a protrusion provided between the storage part and the liquid supplying path, the protrusion configured to form an inner surface gradually narrowed from the storage part to the liquid supplying path, and
   a cap to cover the nozzle,
   wherein the protrusion is configured to block communication between the storage part and the liquid supplying path by abutting inner surfaces thereof causing the constriction part to be flattened,
   wherein the valve is opened to communicate the storage part with an outside of the nozzle and to jet the portion of the liquid to the outside by an internal pressure of the storage part generated by the elastic force of the constriction part when the internal pressure exceeds a predetermined pressure by an elastic force of the constriction part causing the constriction part to be flattened after the protrusion blocks the communication, and
   wherein the valve is closed by the elastic force of the constriction part when the internal pressure is released by spouting the portion of the liquid.

2. The container according to claim 1, wherein the nozzle includes a conduit tube that extends from the base into the main body inner cavity to fluidly couple the liquid supplying path to the main body inner cavity.

3. The container according to claim 1, wherein the cap is removably mounted to the main body using a screw closure.

4. The container according to claim 1, wherein the cap is removably mounted to the main body using a hook and recess arrangement.

5. A container with a liquid-squeezing nozzle, comprising:
   a main body, including:
      an opening, and
      an inner cavity to store a liquid:
   a nozzle, mounted to the main body, including:
      a base engaged with the opening and having a liquid supplying path to fluidly couple with the inner cavity;
      a constriction part having rubber elasticity and flexibility, the constriction part comprising a storage part to store a portion of the liquid, a valve which is naturally closed by an elastic force and is opened by an internal pressure of the storage part generated by an elastic force of the constriction part, and a connecting path configured to connect the storage part to the liquid supplying path, the connecting path having an inner surface which is gradually narrowed from the storage part to the liquid supplying path; and
   a cap, to cover the nozzle,
      wherein the storage part is configured to be fluidly coupled to the main body inner cavity when the constriction part is not flattened,
      wherein the storage part is configured not to be fluidly coupled to the inner cavity when the constriction part is flattened,
      wherein the valve is configured to jet the portion of the liquid into the atmosphere when the constriction part is flattened, and the internal pressure within the storage part exceed a predetermined pressure, and
      wherein the valve is configured to close when the internal pressure is released by spouting the portion of the liquid,
   the container further comprising a pair of flexible levers, symmetrically positioned around the constriction part, to flatten the constriction part when squeezed together.

6. The container according to claim 5, wherein the valve is composed by cross slit which fits to be closed and has width respectively smaller than a squirt direction that the liquid passes.

7. The container according to claim 5, wherein the valve is a pin hole.

8. The container according to claim 5, wherein the nozzle includes a conduit tube that extends from the base into the main body inner cavity to fluidly couple the liquid supplying path to the main body inner cavity.

9. The container according to claim 5, wherein the cap is removably mounted to the main body using a screw closure.

10. The container according to claim 5, wherein the cap is removably mounted to the main body using a hook and recess arrangement.

* * * * *